US007100449B2

(12) United States Patent
Busch et al.

(10) Patent No.: US 7,100,449 B2
(45) Date of Patent: Sep. 5, 2006

(54) METHOD AND APPARATUS FOR COUPLING ULTRASOUND BETWEEN AN ULTRASONIC TRANSDUCER AND AN OBJECT

(75) Inventors: Ralph E. Busch, Loma Linda, CA (US); James C. McKeon, Woodbridge, VA (US); Rodolfo Cruz, Springfield, VA (US)

(73) Assignee: Sonix, Inc., Springfield, VA (US)

( * ) Notice: Subject to any disclaimer, the term of this patent is extended or adjusted under 35 U.S.C. 154(b) by 0 days.

(21) Appl. No.: 11/004,073

(22) Filed: Dec. 3, 2004

(65) Prior Publication Data

US 2005/0119571 A1    Jun. 2, 2005

Related U.S. Application Data

(63) Continuation-in-part of application No. 10/387,881, filed on Mar. 13, 2003, now Pat. No. 6,895,821.

(60) Provisional application No. 60/396,347, filed on Jul. 16, 2002.

(51) Int. Cl.
*G01N 29/04* (2006.01)

(52) U.S. Cl. ............................. 73/644; 73/618; 73/622

(58) Field of Classification Search .................. 73/618, 73/620, 621, 629, 623, 627, 644, 582, 592, 73/596, 598, 41.2, 41.3, 41.4, 622, 624, 642
See application file for complete search history.

(56) References Cited

U.S. PATENT DOCUMENTS

| | | | |
|---|---|---|---|
| 3,063,290 A * | 11/1962 | Kaserman et al. ............ 73/622 |
| 3,489,608 A | 1/1970 | Jacobs et al. | |
| 3,558,093 A | 1/1971 | Bok | |
| 3,617,045 A | 11/1971 | DaCosta et al. | |
| 3,678,735 A * | 7/1972 | Boulanger et al. ............ 73/640 |
| 3,737,573 A | 6/1973 | Kessler | |
| 3,760,822 A | 9/1973 | Evans | |
| 3,765,431 A | 10/1973 | Jannett et al. | |
| 3,790,281 A | 2/1974 | Kessler et al. | |
| 3,850,027 A | 11/1974 | Nakanishi et al. | |
| 3,886,793 A | 6/1975 | Cramer et at. | |
| 3,898,839 A | 8/1975 | White | |
| 3,988,196 A | 10/1976 | Wanesky | |
| 4,008,602 A | 2/1977 | Love | |
| 4,012,951 A | 3/1977 | Kessler | |
| 4,058,000 A | 11/1977 | Ries et al. | |
| 4,164,150 A | 8/1979 | Ries et al. | |
| 4,208,915 A | 6/1980 | Edwards | |
| 4,238,962 A * | 12/1980 | Taenzer ...................... 73/633 |
| 4,252,125 A | 2/1981 | Iinuma | |
| 4,316,271 A | 2/1982 | Evert | |
| 4,332,016 A | 5/1982 | Berntsen | |
| 4,344,448 A | 8/1982 | Potts | |
| 4,472,975 A * | 9/1984 | Beck et al. ................... 73/644 |
| 4,517,985 A | 5/1985 | Teslawski et al. | |
| 4,518,992 A | 5/1985 | Kessler et al. | |
| 4,526,038 A | 7/1985 | Box et al. | |
| 4,543,130 A * | 9/1985 | Shwartzman .................. 134/1 |

(Continued)

*Primary Examiner*—Hezron Williams
*Assistant Examiner*—Jacques Saint-Surin

(57) ABSTRACT

A method and apparatus are disclosed for coupling ultrasound between an ultrasonic transducer and an object. A fluid cavity in an upper chamber has an inlet for receiving a flow of coupling fluid, a first aperture for admitting the ultrasonic transducer into the fluid cavity and a second aperture for dispensing coupling fluid from the fluid cavity to the object. The first and second apertures may be sized to restrict flow of coupling fluid from the fluid cavity. The focus of the ultrasound transducer may be varied by moving the ultrasonic transducer relative to the upper chamber.

33 Claims, 8 Drawing Sheets

U.S. PATENT DOCUMENTS

| | | |
|---|---|---|
| 4,662,215 A | 5/1987 | Eckert |
| 4,781,067 A | 11/1988 | Cichanski |
| 4,807,634 A | 2/1989 | Enjoji et al. |
| 4,854,337 A | 8/1989 | Bunkenburg et al. |
| 4,866,986 A | 9/1989 | Cichanski |
| 4,920,803 A | 5/1990 | Karaki et al. |
| 4,924,707 A | 5/1990 | Kliesch |
| 4,977,779 A | 12/1990 | Karaki et al. |
| 5,014,711 A | 5/1991 | Nagasaki |
| 5,060,517 A | 10/1991 | Fushimi et al. |
| 5,077,695 A | 12/1991 | Khuri-yakub et al. |
| 5,117,697 A | 6/1992 | Takishita et al. |
| 5,195,729 A | 3/1993 | Thomas et al. |
| 5,212,987 A | 5/1993 | Dransfeld et al. |
| 5,240,522 A | 8/1993 | Tanaka et al. |
| 5,301,552 A | 4/1994 | Nagura et al. |
| 5,320,225 A | 6/1994 | Kirkpatrick |
| 5,359,895 A | 11/1994 | Isenberg et al. |
| 5,374,021 A | 12/1994 | Kleinman |
| 5,374,829 A | 12/1994 | Sakamoto et al. |
| 5,431,054 A | 7/1995 | Reeves et al. |
| 5,469,742 A | 11/1995 | Lee et al. |
| 5,531,119 A | 7/1996 | Meyers |
| 5,585,564 A | 12/1996 | Brunty et al. |
| 5,600,068 A | 2/1997 | Kessler et al. |
| 5,629,865 A | 5/1997 | Roth |
| 5,646,351 A | 7/1997 | Good et al. |
| 5,668,452 A | 9/1997 | Villarreal et al. |
| 5,684,252 A * | 11/1997 | Kessler et al. ......... 73/618 |
| 5,874,319 A | 2/1999 | Dunaway et al. |
| 5,922,961 A | 7/1999 | Hsu et al. |
| 5,948,985 A | 9/1999 | Brautigan et al. |
| 5,996,415 A | 12/1999 | Stanke et al. |
| 6,027,605 A | 2/2000 | Lehmann et al. |
| 6,062,084 A | 5/2000 | Chang et al. |
| 6,085,591 A | 7/2000 | Mallard |
| 6,089,095 A | 7/2000 | Yang et al. |
| 6,227,946 B1 | 5/2001 | Gonzalez-Martin et al. |
| 6,230,896 B1 | 5/2001 | Lambert |
| 6,261,370 B1 | 7/2001 | Otsuki et al. |
| 6,357,136 B1 * | 3/2002 | Erickson et al. ......... 34/60 |
| 6,460,414 B1 | 10/2002 | Erickson et al. |
| 6,513,796 B1 | 2/2003 | Leidy et al. |
| 6,524,351 B1 | 2/2003 | Ohta |
| 6,540,014 B1 | 4/2003 | Getchel et al. |
| 6,554,003 B1 | 4/2003 | Birang et al. |
| 6,603,103 B1 | 8/2003 | Ulrich et al. |
| 6,709,877 B1 | 3/2004 | Tsui et al. |
| 6,743,296 B1 | 6/2004 | Kao |
| 6,880,387 B1 | 4/2005 | Kessler et al. |
| 6,890,302 B1 | 5/2005 | Oravez et al. |
| 6,895,820 B1 | 5/2005 | Oravez et al. |
| 6,912,908 B1 | 7/2005 | Kessler et al. |
| 6,921,672 B1 | 7/2005 | Satya et al. |
| 2004/0011133 A1 * | 1/2004 | Busch et al. |

* cited by examiner

METHOD AND APPARATUS FOR COUPLING ULTRASOUND BETWEEN AN ULTRASONIC TRANSDUCER AND AN OBJECT

CROSS REFERENCE TO RELATED APPLICATIONS

This application is a continuation in part of U.S. patent application Ser. No. 10/387,881 filed Mar. 13, 2003 now U.S. Pat. No. 6,895,821 and titled "Ultrasonic Test Chamber for Tray Production System and the Like" and claims priority to and benefit of the earlier filing date of U.S. application Ser. No. 10/387,881, as well as to U.S. Provisional Application No. 60/396,347, filed Jul. 16, 2002 from which U.S. application Ser. No 10/387,881 claims priority.

FIELD

This invention relates generally to the field of ultrasonic scanning. More particularly, this invention relates to a method and apparatus for providing acoustic coupling between an ultrasonic scanner and a test piece.

BACKGROUND

Non-destructive inspection of parts has been used for many years. More recently, ultrasonic inspection has been extended to small parts such as integrated circuits or other electronic components. During the manufacture of integrated circuits (ICs), the parts are often loosely arranged in trays or holders to facilitate transfer of the parts through the production process. In order to prevent delays in the production process, an ultrasonic tester that can accommodate trays of parts is required.

An ultrasonic tester may include three sections. The first section is a de-bubbling area where the parts in the carriers are wetted and air bubbles are removed. The normal convention is to submerge the parts and 'wiggle' them to remove the air bubbles. The second section is a scanning station where wetted and bubble free parts are ultrasonically scanned. In order to complete the scan in a short time, the ultrasonic transducer must be moved across the parts at high speed in close proximity to the parts. The result is a motion in the fluid that tends to move the parts in the carriers or dislodge them from the carrier. The third section is a drying area, where a gas stream is used to dry any residual coupling fluid from the parts. Typically compressed and/or heated air is directed across the parts. Each of these processes tends to dislodge the parts when they are loosely arranged in a tray or carrier.

There is a continuing drive towards the use of higher frequency ultrasound, which provides greater resolution of the scanned image. Since higher frequency ultrasound is attenuated in very short distances, it is necessary to move the ultrasonic transducer very close to the object being scanned. Conventional, non-immersion, transducer may be fitted with squirters or bubbles that produce a column of coupling fluid between the transducer and the part. These do not allow the transducer to be moved close enough to the part to prevent the attenuation of very high frequency ultrasound.

SUMMARY

The present invention relates generally to ultrasonic scanning. Objects and features of the invention will become apparent to those of ordinary skill in the art upon consideration of the following detailed description of the invention.

The invention relates to methods and apparatus for coupling ultrasound between an ultrasonic transducer and an object. A fluid cavity in an upper chamber has an inlet for receiving a flow of coupling fluid, a first aperture for admitting the ultrasonic transducer into the fluid cavity and a second aperture for dispensing coupling fluid from the fluid cavity to the object. The first and second apertures may be sized to restrict flow of coupling fluid from the fluid cavity. The focus of the ultrasound transducer may be varied by moving the ultrasonic transducer relative to the upper chamber.

BRIEF DESCRIPTION OF THE DRAWINGS

The novel features believed characteristic of the invention are set forth in the appended claims. The invention itself, however, as well as the preferred mode of use, and further objects and advantages thereof, will best be understood by reference to the following detailed description of an illustrative embodiment when read in conjunction with the accompanying drawing(s), wherein:

DETAILED DESCRIPTION

Figure 1:
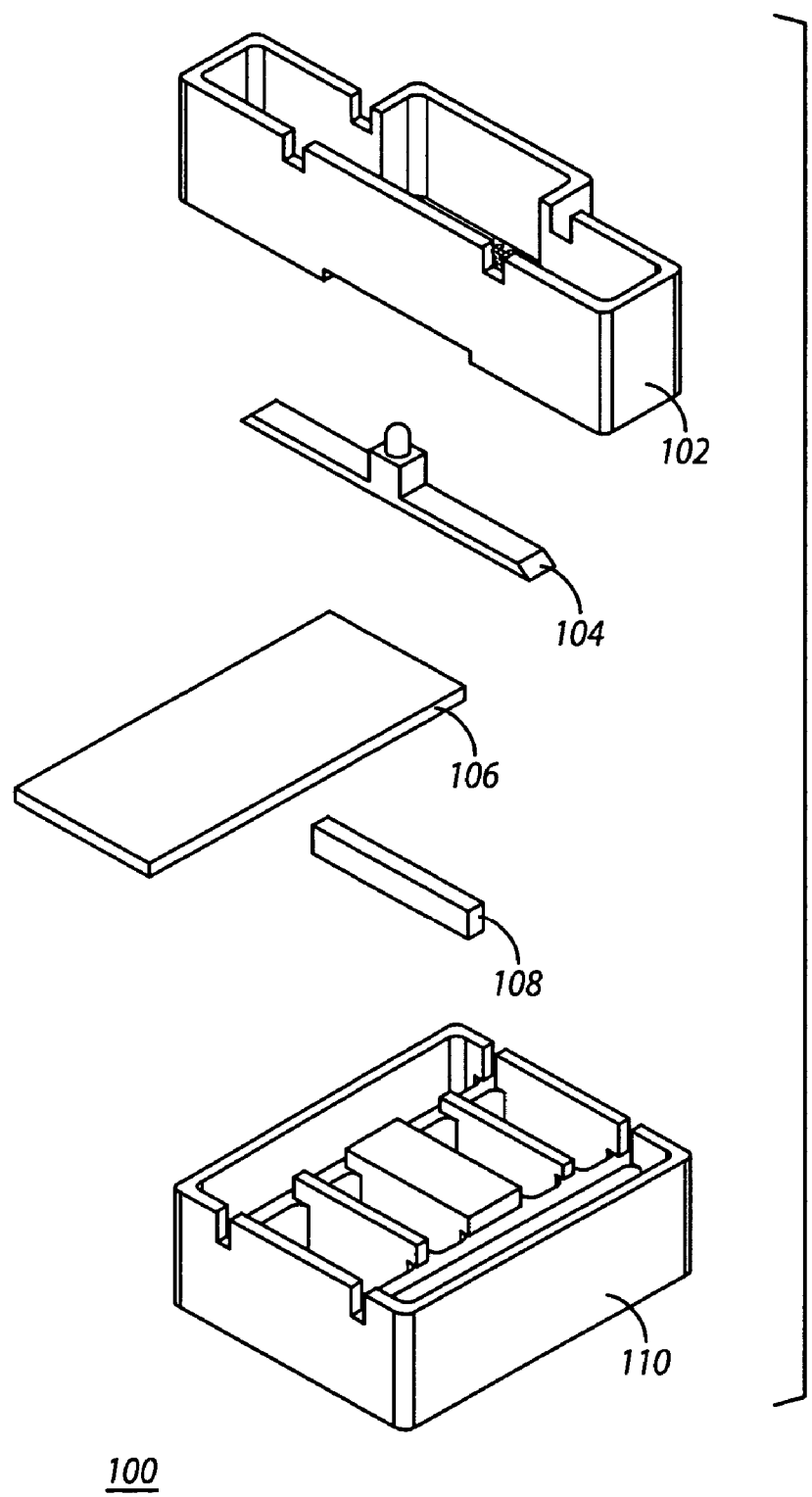
FIG. 1 is an exploded view of an ultrasonic test chamber in accordance with certain embodiments of the present invention.

While this invention is susceptible of embodiment in many different forms, there is shown in the drawings and will herein be described in detail one or more specific embodiments, with the understanding that the present disclosure is to be considered as exemplary of the principles of the invention and not intended to limit the invention to the specific embodiments shown and described. In the description below, like reference numerals are used to describe the same, similar or corresponding parts in the several views of the drawings.

One aspect of the present invention is a method and a system for ultrasonic scanning of parts in which coupling fluid is used to hold parts in a parts holder or tray. A further aspect of the invention is method and system for holding parts in a parts holder while bubbles are removed from parts before they are scanned. Still further aspects of the invention will be apparent from the following detailed description of illustrative embodiments.

In one embodiment, the ultrasonic test chamber of the present invention includes three functional sections: a de-bubbling station, a scanning station and a dryer. FIG. 1 shows an exploded view of an exemplary test chamber 100 in accordance with the invention. The test chamber comprises a lower chamber 110 and an upper chamber 102. The chambers are held by a frame or housing (not shown) so that the gap between the two chambers may be adjusted to accommodate trays of varying thickness. In this embodiment, the lower chamber is fixed and the upper chamber may be raised or lowered. The upper chamber houses a moveable plate or scanning bar 104, the bottom of which is flush with the bottom of the upper chamber. A first ultrasonic transducer is mounted in the scanning bar and can be independently moved up or down (relative to the lower chamber and relative to the scanning bar) to place the transducer at the proper distance from the parts. During operation, a parts tray 106 is passed beneath the transducer and plate. A second ultrasonic transducer 108 may be mounted in the lower chamber 110 beneath the tray of parts 106, so that transmission of ultrasound through the parts may be measured. The first or second transducers may, for example, comprise a single element transducer having a spot, line or flat focus, an array of transducers, one or more array transducers or a combination thereof. The arrays may be line arrays having a single dimension, or area arrays having two dimensions. Example transducers include the Panametrics V313 crystal transducer, the Sonix MSIC-75M S-12 polymer transducer, the Panametrics V3815 crystal, delay-line transducer, the Panametrics A334S-SU paintbrush transducer, the Krautkramer linear array and the Imperium DAV area array.

Figure 2:
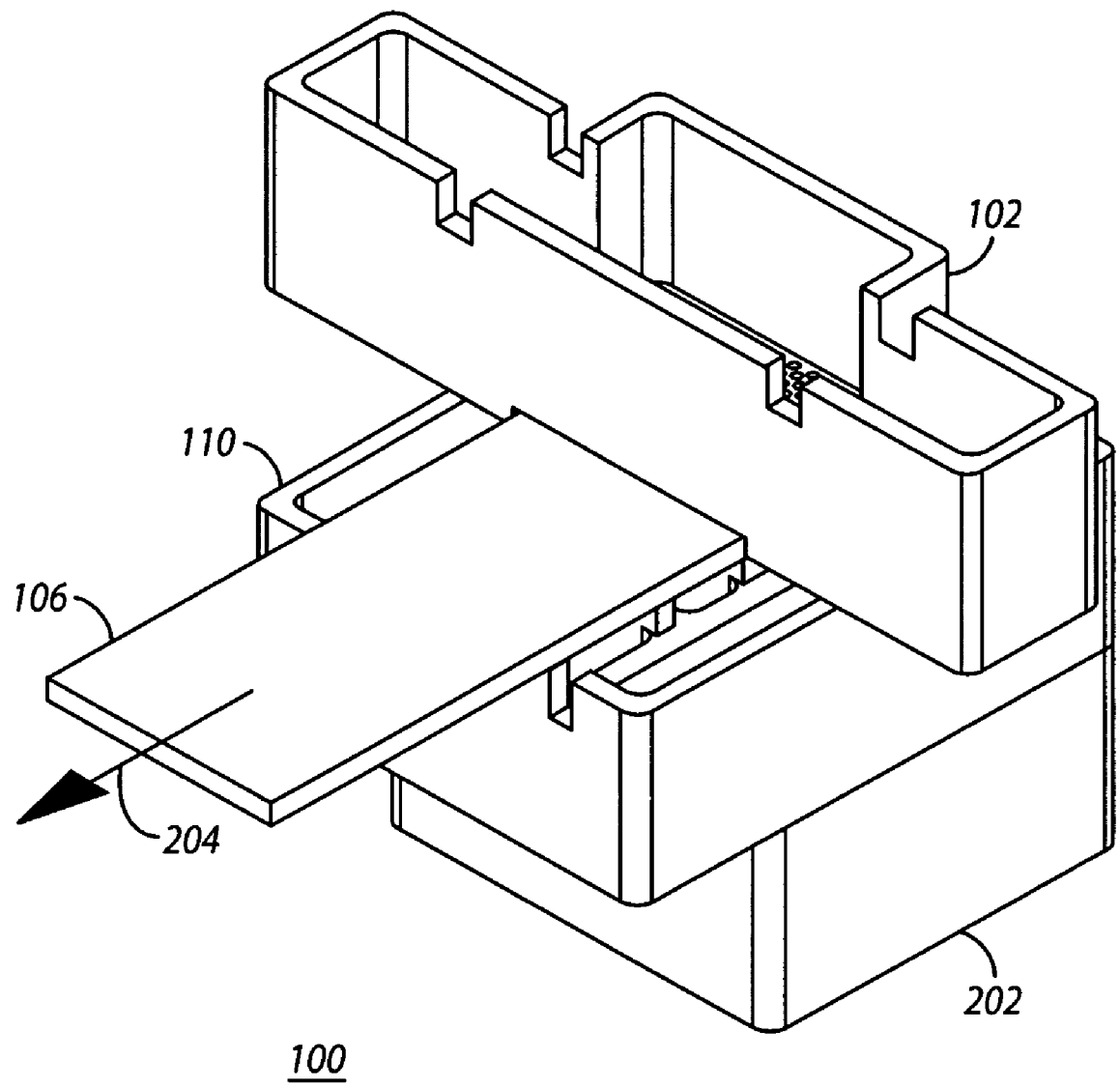
FIG. 2 is a further view of the ultrasonic test chamber shown in FIG. 1.

An assembled ultrasonic test chamber 100 is shown in FIG. 2. The upper chamber 102 is supported by a frame (not shown) so that the moveable plate or scan bar (104 in FIG. 1) is in close proximity to the upper surface of the parts in the tray of parts 106. The tray of parts 106 is moved in the direction of arrow 204 along a track, entering the right side of the chamber in the figure and exiting the left side. The tray may be propelled along the track by an arm connected to a screw drive, for example. The upper and lower chambers are kept filled with a coupling fluid. Fluid is added at rate sufficient to compensate for the fluid lost through openings in the upper and lower chambers. Spilled fluid may be collected in a reservoir 202 and used to the refill the chambers. The re-filling can be performed by a pump so that fluid is re-circulated from the reservoir to the upper and lower chambers. In this manner, the tray of parts may be maintained in a substantially horizontal position.

Figure 3:
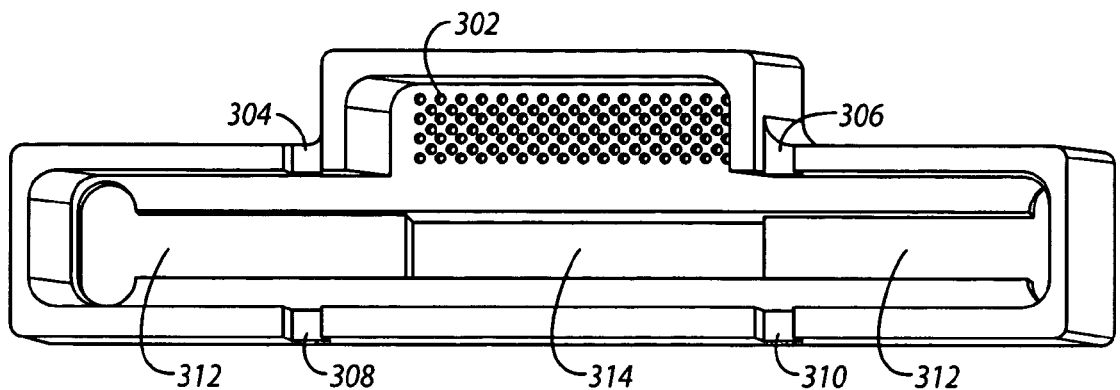
FIG. 3 is a diagrammatic representation of an upper chamber of an ultrasonic test chamber.

Fluid flow through the tray of parts is restricted, so fluid may be added to the tray from the upper chamber at a rate sufficient to maintain sufficient fluid in the tray to permit acoustic coupling of the ultrasonic beam to the top of the parts in the tray. If measurement of transmission through the part is not required, the lower chamber may be omitted or replaced with a fluid-capture tray. A more detailed view of the upper chamber 102 is shown in FIG. 3. The chamber is viewed from above. In use, the tray of parts first passes below a region of perforations or holes 302. In a further embodiment, the region 302 may contain a single slot. Region 302 is the de-bubbling region. Fluid is passed from below the parts and directed toward the underside of the parts so as to remove air bubbles. Excess fluid passes through the perforations or one or more slots 302 and enters the upper chamber. Additional fluid may be added to the upper chamber as required. The perforations or slots are sized so as prevent the parts from being dislodged by the fluid flow. Excess fluid may escape through one or more channels 304, 306, 308, 310, or through drain pipes (not shown). A track 312 is provided to guide the scanning bar 104. The scanning bar slides from left to right and right to left with the first transducer as it traverses the parts in the tray. The ultrasonic beam or transducer passes through opening 314. The parts in the tray are held in place by the scanning bar. In a further embodiment, the de-bubbling area and the scanning area may be separated.

Figure 4:
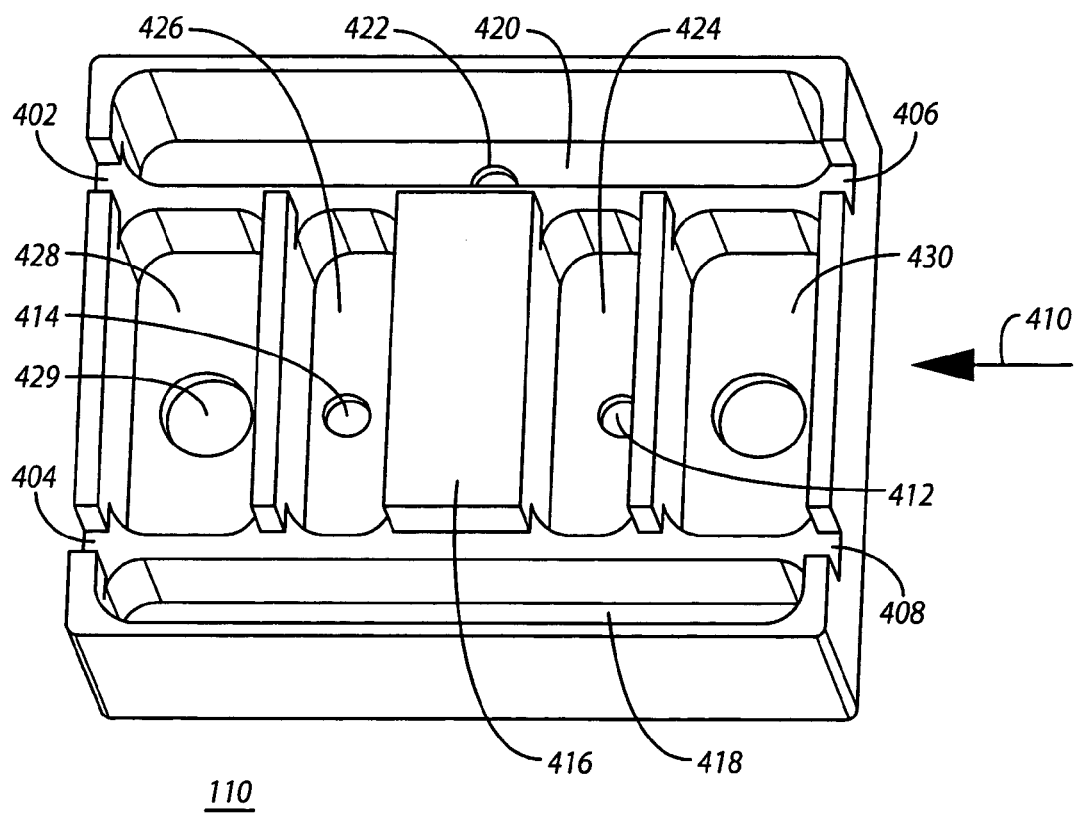
FIG. 4 is a diagrammatic representation of a lower chamber ultrasonic test chamber bottom.

A more detailed view of the lower chamber 110 is shown in FIG. 4. The chamber is viewed from above. In use, the tray of parts enters on the right of the figure, moving in the direction of arrow 410. The lower chamber is positioned below the tray of parts 106 (not shown). The tray of parts moves along a track. One rail of the track lies in the slot between openings 402 and 406, the other lies in the slot between opening 404 and 408. In the embodiment shown in FIG. 4, the lower tray is symmetric so that parts may enter from the left or the right. If parts enter from the left, the upper chamber is rotated through 180°. The following description assumes that trays enter from the right in the figure. Chamber 430 is a copy of chamber 428 and is included to permit reversal of the tray movement. It is not necessary. De-bubbling chamber 424 is positioned below the de-bubbling region (302) of the upper chamber. Fluid is injected into the de-bubbling chamber 424 through hole 412. The fluid may be injected at multiple locations. The injected fluid serves to dislodge air bubbles adhering to the underside of the parts in the tray. The tray then passes over raised region 416. Preferably the raised region is a substantially planar surface. This surface prevents the turbulence from the fluid in chamber 424 from reaching the scanning region, it also tends to reduce fluid flow, facilitating the ultrasonic coupling between the transducer and the parts in the tray. The scanning region may be above the raised region 416 or to the left of the raised region. If a second transducer is employed, it may be embedded in the raised region or positioned immediately to the left of the raised region. Drain chamber 426 is positioned after the scanning region. Fluid is drained from this region through opening 414. The region will typically contain both fluid and air, and will allow the underside of the parts to begin to dry. Fluid flows from the de-bubbling chamber 424 to the drain chamber 426, thereby maintaining a flow of fluid from right to left across the raised region 416. This flow, combined with the column of fluid above the parts being scanned, helps to keep the parts in place. Finally the tray of parts enters the drying region above chamber 428. Air suction may be applied at opening 429 to help hold the parts in place. The parts are then dried by an air knife, hot air, a brush or by wicking materials (or a combination thereof). The brush or wicking materials are attached to the top side of the lower chamber or to the support frame. Side chambers 418 and 420 collect fluid spilled from the sides of the center chambers (424 and 426) and contain drain holes (422 for example) to allow the spilled fluid to be captured in the reservoir.

In a further embodiment, the upper and lower chambers may be integrated, and height of the flat plate varied to accommodate trays of varying thickness.

Figure 5:
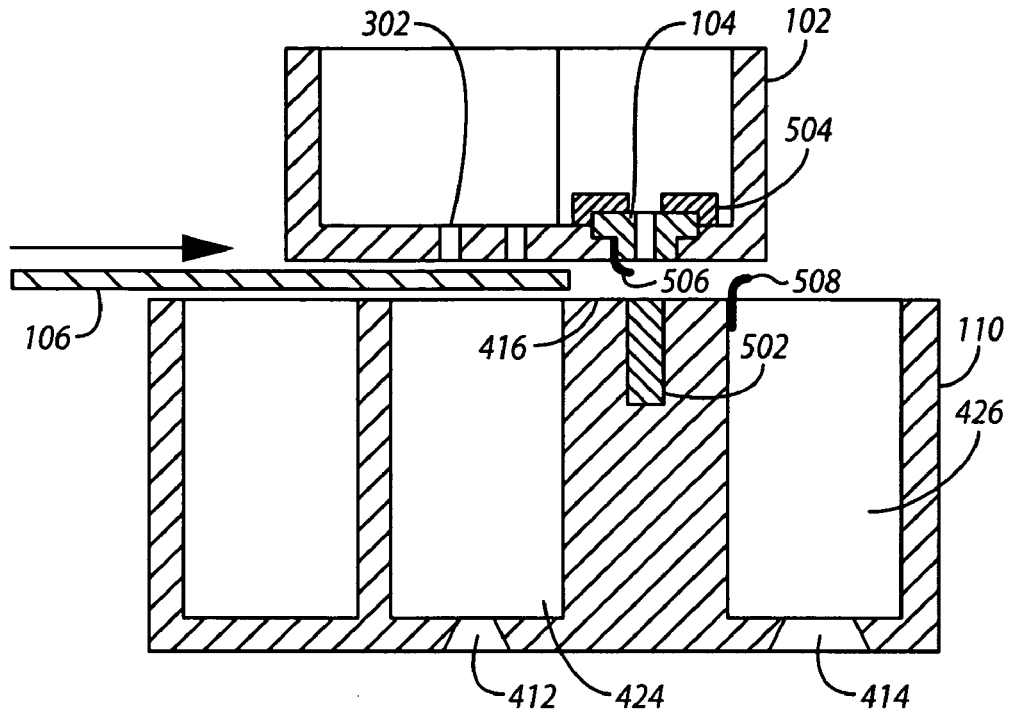
FIG. 5 is a cross sectional diagram of an ultrasonic test chamber in accordance with certain embodiments of the present invention.

FIG. 5 shows a cross-sectional diagram of an exemplary ultrasonic test chamber. A vertical cross-sectional along the axis of motion of the parts tray 106 is shown. The parts tray moves from left to right in the figure. The lower chamber 110 includes a de-bubbling chamber 424 with opening 412 to receive a flow of fluid. In this embodiment, a second transducer 502 is embedded in the raised region 416 to permit through-transmission measurements. The drying chamber 426 includes opening 414 where air suction may be applied to hold the parts in place while they are dried. The upper chamber 102 includes at least one opening 302 through which fluid from the de-bubbling chamber passes. The moving flat plate or scanning bar 104 includes an opening to accommodate the first transducer. A brace or bracket 504 may be used to prevent movement of the flat plate in directions other than the scan direction. Preferably the scan direction is in a horizontal plane perpendicular to the motion of the tray, although skewed scan directions may be used. A set of spring fingers 506 may be used to hold the parts in place while scanning is performed. The spring fingers 506 are attached to the upper chamber 102 and extend downwards and in the direction of motion of the tray. As the tray passes under the spring fingers they are displaced upwards and exert a downward spring force on the parts in the tray. A brush or wicking material 508 is attached to the lower chamber to remove water droplets from the bottom surface of the parts in the tray.

Figure 6:
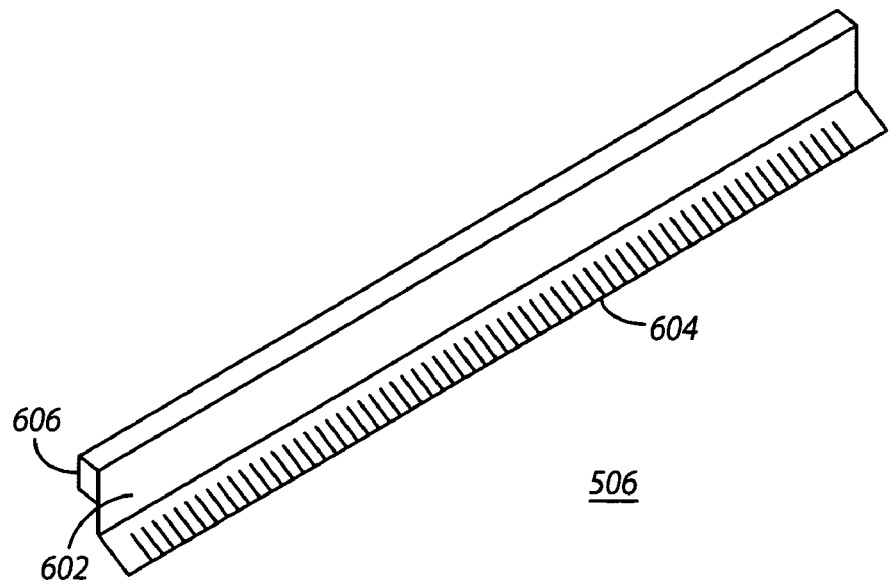
FIG. 6 is a diagrammatic representation of an array of spring fingers in accordance with certain embodiments of the present invention.

A more detailed view of the spring fingers 506 is shown in FIG. 6. In this embodiment, a sheet of metal 602 is bent to form an angle. Slots 604 are formed in the metal on one side of the fold. The material between the slots forms the spring fingers. Projection 606 may be included to facilitate attachment of the set of the spring fingers to the upper chamber.

A more detailed description of the operation is given below, together with some alternative embodiments.

DE-BUBBLING AREA. The de-bubbling area is where the parts in the carriers are wetted and air bubbles are removed. Several aspects of the de-bubbling area are now described.

Side Fluid Penetration. The test chamber of the present invention is partially filled with a coupling fluid, such as water, to facilitate coupling of the ultrasonic beam to the part under test. The test chamber has one or more openings in the sides, below the level of the fluid, to allow a parts carrier to passing into the chamber. In one embodiment, this opening is the gap between the upper and lower chambers. Since fluid will leak from the opening, additional fluid is passed into the chamber to maintain the fluid level. Preferably, the fluid leaking from the one or more openings is collected and returned to the chamber. The carrier does not have to be raised or lowered, so the system is compatible with production line configurations and handling equipment.

Water Jet. To remove any air bubbles adhering to the parts, a stream of water or other fluid is forced across the parts. Preferably, the flow of water is from bottom to top because that is the directions the air bubbles will float when separated from the part or carrier.

Perforated or Slotted Cover. In the case where the water jet is flowing upward, the water will tend to dislodge the parts from the carrier. A perforated or slotted cover is used to hold the parts in the carrier. The holes are large enough to let water and air bubbles pass but small enough so that parts can not pass or be dislodged.

SCANNING STATION. The scanning station is where wetted and bubble free parts are ultrasonically scanned. The ultrasonic transducer is moved across the parts at high speed in close proximity to the parts. The result is a motion in the fluid that tends to move the parts in the carriers or dislodge them from the carrier. For though-transmission (TT) tests, separate transducers or arrays of transducers are used above and below the carrier. The scanning station of the present invention uses one or more of the following approaches to hold the parts in the holder:

Carriers with Retaining Clips. In a first embodiment of the present invention, a carrier with retaining clips is used to prevent the parts in the carriers from being dislodged. In some areas of the semiconductor part manufacturing process, it is advantageous to hold the parts in a carrier with a retaining clip. For example, the Auer Company manufactures metal carriers commonly referred to as boats that have retaining clips (For example, Auer part number A27150-001 manufactured in 9/00 per drawings 110892 Rev. B). Boats can be used in curing ovens and other stages of semiconductor manufacturing. Current practice is to remove the parts from these "boats" and place them in JEDEC trays before scanning ultrasonically. By scanning the parts in the "boats" the parts do not have to be moved to another carrier and the parts are held in place during the ultrasonic scan.

High Pressure above Carrier. In one embodiment of the invention, fluid is added to the parts carrier from above. The fluid is added at one or more positions away from the scanning area, so that fluid flow does not tend to dislodge the parts. Furthermore, since flow through the parts carrier is restricted, the static fluid pressure above the parts is higher than the pressure below the parts. This results in a net downward force acting to hold parts in the part carrier. Thus, the coupling fluid tends to hold the parts in place rather than to dislodge them.

Low Pressure under Carrier. Because any motion in the fluid (caused for example by transducer movement) around the parts may tend to move the part in the holder during the scan (which results in a blurred ultrasonic image) or dislodge the part entirely from the holder, it is desirable to have some type of force holding the parts in to holder. Since materials other than the coupling fluid (typically de-ionized water) will have different acoustic impedances and degrade the ultrasonic image, it is desirable for this force to be applied via the coupling fluid. In one embodiment of the invention a fluid flow is maintained below the carrier. This results in a net downward force on the parts that will tend to hold the parts in the carrier. The flow is maintained across the raised region of the lower chamber.

Figure 7:
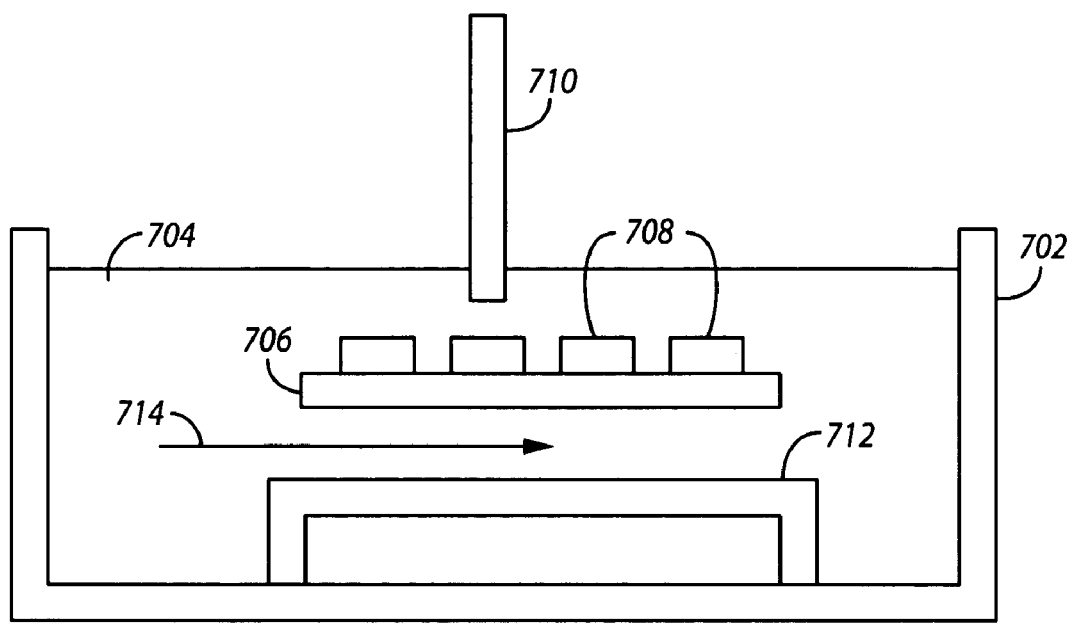
FIG. 7 is a cross sectional diagram of an ultrasonic test chamber in accordance with further embodiments of the present invention.

FIG. 7 is a simplified cross-sectional diagram of an ultrasonic test chamber in accordance with a further embodiment of the present invention. In this embodiment, the scanning station comprises a tank 702 containing coupling fluid 704. A tray 706 supports a number of objects 708. Typically, the objects are loosely held. An ultrasonic transducer 710 is used to scan the objects. A second transducer (not shown) may be used to sense the ultrasound transmitted through the objects. The holder or tray 706 is held above a surface 712. Preferably, the surface is flat in the direction of the scan line of the ultrasonic transducer 710, but may be curved in the other direction to facilitate fluid flow. A flow of coupling fluid is generated in the direction of the arrow 714, between the surface 712 and the underside of the tray 706. This flow produces a lower pressure beneath the tray. The pressure differential across the object in tray results in a net downward force on the object and holds the object in the tray, and prevents it from being dislodged by turbulence produced by motion of the ultrasonic transducer or the tray. The flow may be generated, for example, by fluid jets acting on one side of the tray or by suction acting on one side of the tray.

Figure 8:
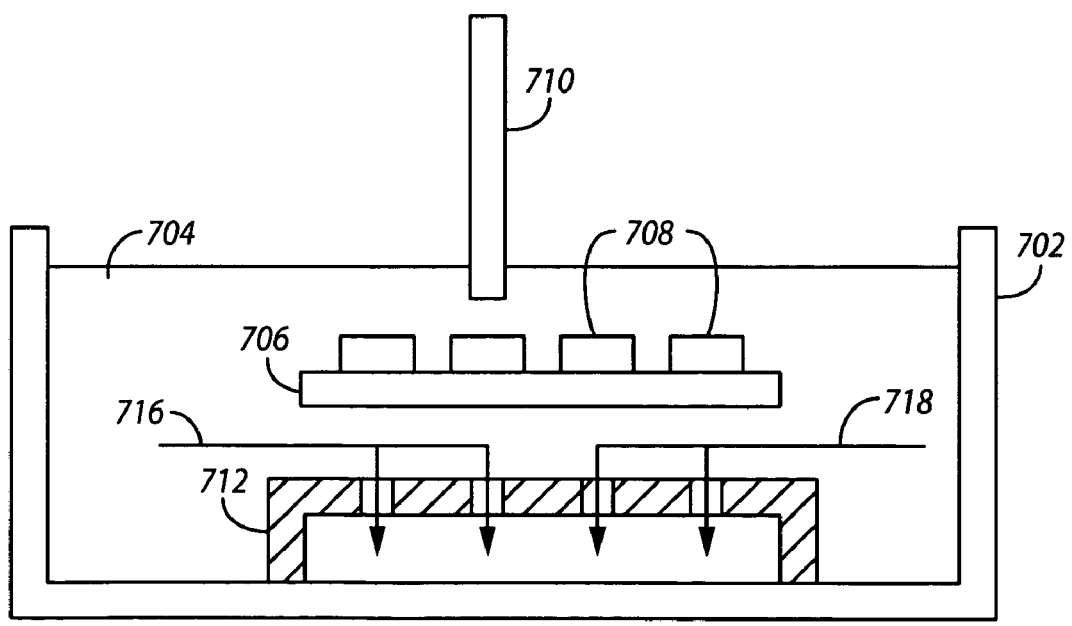
FIG. 8 is a cross sectional diagram of an ultrasonic test chamber in accordance with still further embodiments of the present invention.

FIG. 8 is a simplified cross-sectional diagram of a ultrasonic test chamber in accordance with a still further embodiment of the present invention. In this embodiment, the scanning station comprises a tank 702 containing coupling fluid 704. A tray 706 supports a number of objects 708. Typically, the objects are loosely held. An ultrasonic transducer 710 is used to scan the objects. A second transducer (not shown) may be used to sense the ultrasound transmitted through the objects. The tray 706 is held above a surface 712. Preferably, the surface is flat in the direction of the scan line of the ultrasonic transducer 710. A flow of coupling fluid is generated in the direction of the arrows 716 and 718, between the surface 712 and the underside of the tray 706. The flow is produced by drawing fluid, from beneath the surface 712, through one or more holes in the surface. This flow produces a lower pressure beneath the tray. The pressure differential across the object in tray results in a net downward force on the object and holds the object in the tray, preventing it from being dislodged by turbulence produced by motion of the ultrasonic transducer or the tray. Other methods for producing a suitable fluid flow will be apparent to those of ordinary skill in the art.

Retaining Strip. In a further embodiment, where additional force is required to hold the parts in the holder at the scanning station, a retaining strip is used. The retaining strip is comprised of a continuous strip or a series of fingers made out of a spring-like material that applies a slight downward pressure to the top of the parts. The fingers are positioned so that they do not cover the parts at the scan line. Two rows of retaining strips, one prior to and one after the scanning line are used.

Scanning Bar (moving cover). In a further embodiment, a flat plate or bar mounted flush with the bottom of the transducer is used to prevent the parts in the holders from being dislodged. The flat plate, referred to as a scanning bar, acts as a barrier between the fluid around the transducer that is disturbed during motion and the fluid surrounding the parts in the holder. This prevents the disturbed fluid from tending to affect the position of the parts. If the scanning bar is kept in close proximity to the top of the holder it will also insure that parts can not leave the holder in the scanning station. To keep the size and mass of the scanning bar small, the scanning bar can be integrated with a stationary cover to insure that the parts cannot leave the holder while in the scanning station.

The above techniques, namely scanning bar, retaining strip, high-pressure and low pressure, can be used in any and all possible combinations.

Fixed through-transmission Transducer. Through-transmission tests typically require a transmitter on one side of the part and a receiver on the other side. Typically, both of these transducers will move together at the same rate and directions. By using a single element or array transducer for either the UT transmitter or receiver, only one of the two transducers will be in motion thereby reducing the disturbance to the fluid around the parts and simplifying the mechanics required to implement a system. In accordance with certain embodiments, the fixed transducer is located below the holder so that the moving transducer can be in closer proximity to the parts which is currently a requirement for the high frequency scans.

Fixed Array (linear and area). If any/all of the ultrasonic transducers required are linear or area arrays the speed required can be reduced thereby reducing the tendency for the parts to move or be dislodged from the holder. In accordance with certain embodiments, the transducers will completely cover the width of a tray and will not be required to move at all. The array could be integrated with a top or bottom cover plate. The array could also be used in conjunction with a fixed through-transmission transducer.

Figure 9:
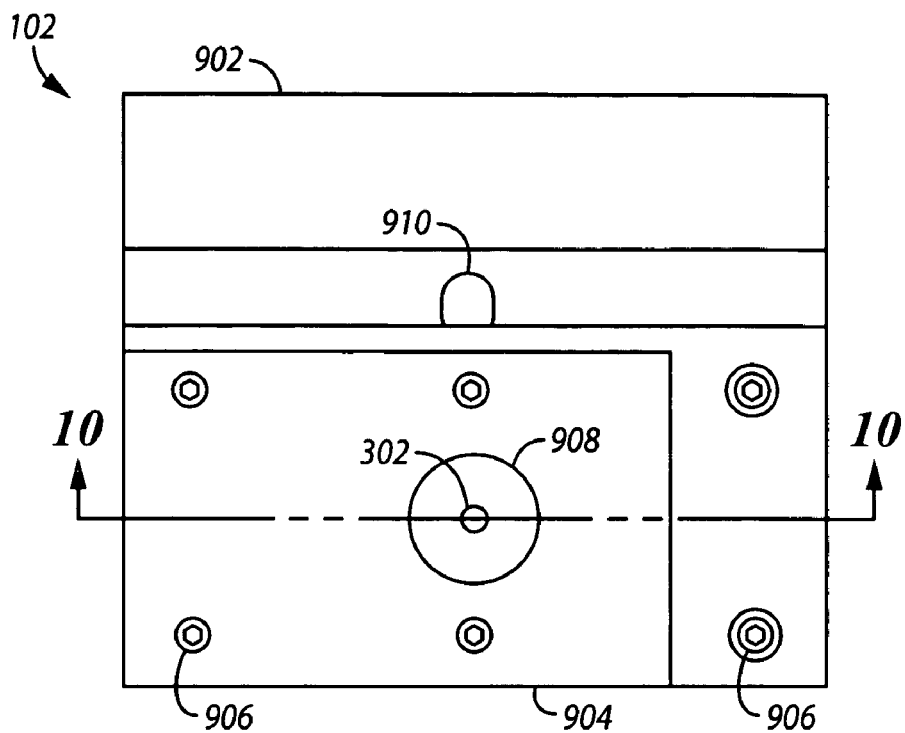
FIG. 9 is top view of a further embodiment of an upper chamber.
Figure 10:
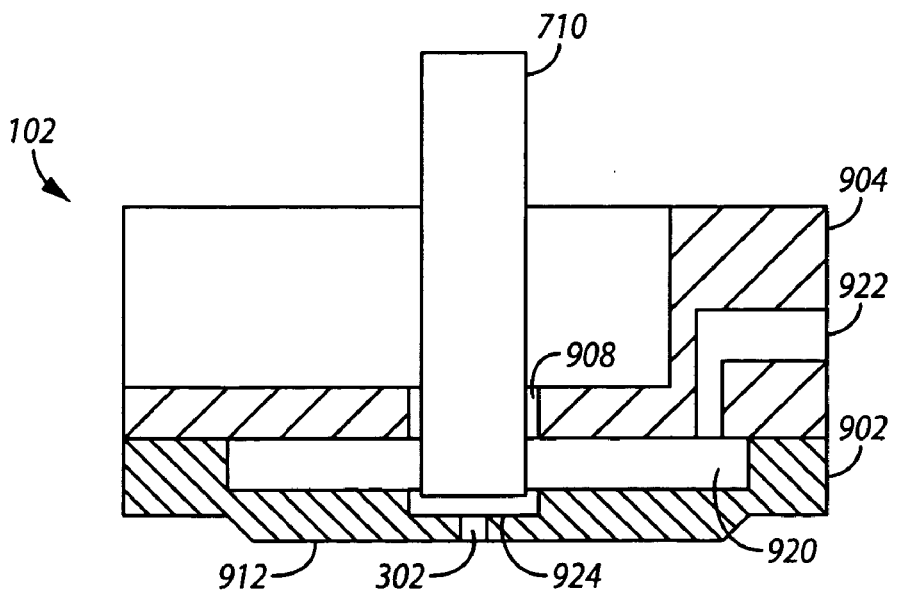
FIG. 10 is a sectional view of the upper chamber shown in FIG. 9.

Integrated Upper Chamber and Scanning Bar. In a further embodiment of the scanner, the upper chamber is moved with the ultrasonic transducer as it is scans the object. This allows the upper chamber and the scanning bar to be combined. An embodiment of the upper chamber is shown in FIG. 9. Referring to FIG. 9, the upper chamber 102 comprises a lower piece 902 and an upper piece 904. The upper and lower pieces may be held together by fasteners, such as screws 906 or by adhesive, for example. An aperture 908 is provided in the upper piece 904 to allow passage of an ultrasonic transducer. An aperture 302 in the lower piece 902 allows for transmission of the ultrasonic beam to the object being scanned. A mounting hole 910 may be provided to allow for a support structure to hold the ultrasonic transducer in alignment with the upper chamber. The section 10—10 is shown in FIG. 10. The use of an upper piece and a lower piece facilitate the manufacture of the upper chamber, however, it will be apparent to those of ordinary skill in the art that the upper chamber may be formed as a single piece or from a plurality of pieces.

A view through the section 10—10 in FIG. 9 is shown in FIG. 10. In FIG. 10, an ultrasonic transducer 710 is shown passing through the aperture 908 in the upper piece 904. The ultrasonic transducer 710 may be moved vertically with respect to the upper chamber 102 to allow for focusing of the ultrasonic beam at different depths in the object under test. This allows the spacing between the upper chamber 102 and part under test to be held substantially constant. A fluid cavity 920 is formed between the upper piece 904 and the lower piece 902. In operation, coupling fluid in moved into the fluid cavity 920 through fluid inlet 922. The coupling fluid exits the fluid cavity 920 through aperture 302 in the bottom of the fluid cavity and through aperture 908 in the top of the chamber. The bottom surface of the fluid cavity 920 may contain a recess 924 sized to accommodate the ultrasound emitting surface of the ultrasonic transducer 710. The thickness of the wall of the fluid cavity in the recess may be less than 1 mm, enabling the ultrasonic transducer 710 to be positioned closer to the object being scanned. This facilitates the use of very high frequency ultrasound (with frequencies from a hundred megahertz to several gigahertz or more). The lower surface of the lower piece 902 may have a lowered section 912. This lowered section 912 serves a similar purpose to the scanning bar described above (104 in FIG. 1).

Figure 11:
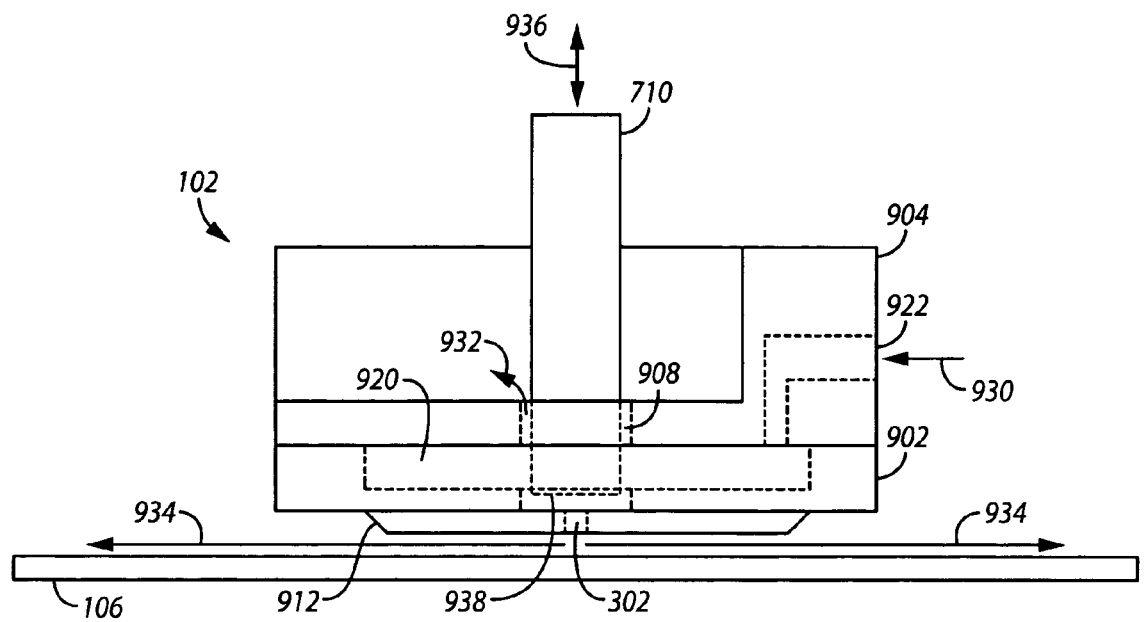
FIG. 11 is a front view of the upper chamber shown in FIG. 9.

FIG. 11 is front view of the upper chamber of FIG. 9. In operation, coupling fluid enters the fluid cavity 920 through fluid inlet 922 in the direction of arrow 930 and exits the fluid cavity 920 through apertures 908 and 302 in the directions of arrows 932 and 934, respectively. The apertures 908 and 302 may be sized such that there is a resistance to fluid flow when the ultrasonic transducer 710 is placed in the aperture 908. This results in an increased pressure in the coupling fluid within the fluid cavity 920. The coupling fluid that exits the aperture 302 in the direction of arrows 934 forms a film or layer of coupling fluid between the lowered surface 912 and the object 106 being scanned. If the spacing between the object 106 being scanned and the lowered surface 912 is small, there will be an increased pressure in the film of coupling fluid between the lowered surface 912 and the object 106. When the object is a loosely held in a tray of parts, this helps to hold the object in the tray. In general, the film of coupling fluid effectively removes bubbles from the surface of the object being scanned. The film of coupling fluid may be less than 1 mm thick, and the ultrasound emitting surface of the ultrasonic transducer may be positioned less than 1 mm from the surface of the object being scanned.

The ultrasonic transducer 710 is moveable vertically with respect to the upper chamber 102 in the direction of arrow 936. This allows the transducer to be focused to different depths within the object 106 being scanned, while allowing the upper chamber 102 to remain at a constant height above the object 106. The ultrasonic transducer 710 may be moved using a linear motion actuator, such as a screw drive. The position of the ultrasonic transducer may be adjusted manually or under computer control. The bottom surface of the fluid cavity 920 may contain a recess 924 sized to accommodate the tip 938 of the ultrasonic transducer 710. This enables the ultrasonic transducer 710 to be positioned closer to the object being scanned and, in turn, allows higher frequency ultrasound to be used.

The flow of coupling fluid from the fluid cavity 920 out through the aperture 908 dislodges bubbles from the tip 938 of the ultrasonic transducer 710 and allows them to exit through the aperture 908.

Figure 12:
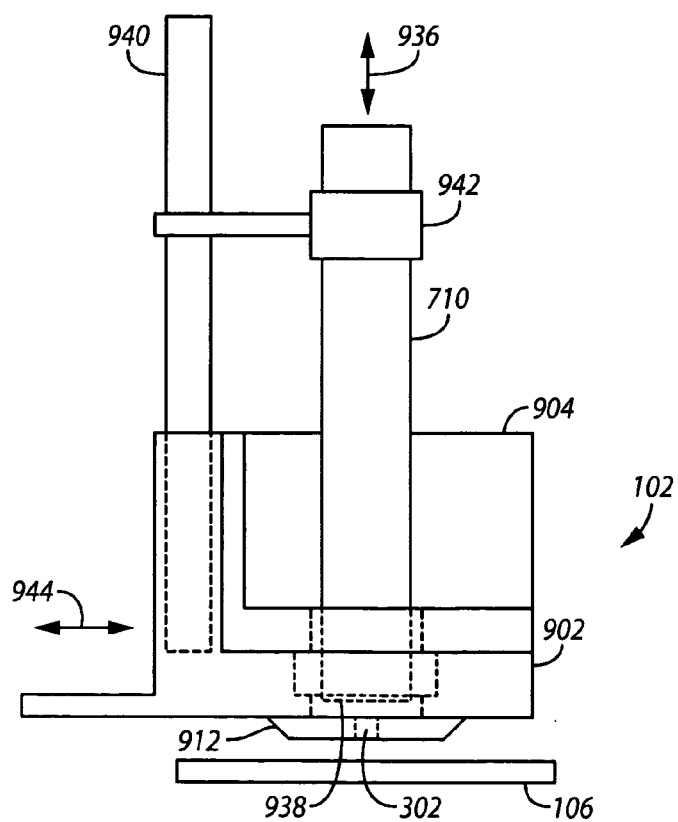
FIG. 12 is a side view of scanning apparatus using the upper chamber shown in FIG. 9.

FIG. 12 is a side view of a scanning apparatus using the upper chamber 102. Referring to FIG. 12, a linear motion device 940, such as screw drive, is attached to the upper chamber 102. A bracket 942 holds the ultrasonic transducer 710 and couples it to the linear motion device 940. This allows the ultrasonic transducer 710 to be moved in direction of arrow 936 to focus the ultrasound at the desired depth in the object 106 being scanned. In this embodiment, the ultrasonic transducer 710, linear motion device 940 and upper chamber 102 are moved in a horizontal scanning path parallel to the upper surface of the object 106, as indicated by the arrow 944 using one or more additional motion actuators (not shown). Additionally, or alternatively, the object 106 may be moved beneath upper chamber 102. For example, the upper chamber 102 and the object 106 may be moved in perpendicular horizontal paths to allow the upper surface of the object to be scanned.

Figure 13:
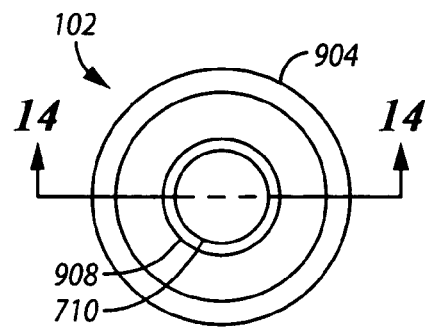
FIG. 13 is top view of a still further embodiment of an upper chamber.
Figure 14:
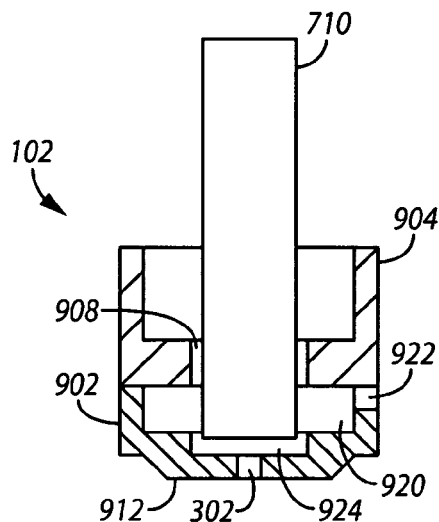
FIG. 14 is a sectional view of the upper chamber shown in FIG. 13.

An alternative embodiment of an upper chamber 102 is shown in FIGS. 13 and 14. FIG. 13 is a top view of the upper chamber 102 showing an upper piece 904. An ultrasonic transducer 710 passes through an aperture 908 in the upper piece 904. FIG. 14 is sectional view through the section 14—14 shown in FIG. 13. FIG. 14 shows upper piece 904 and lower piece 902 that together form the fluid cavity 920. In operation, coupling fluid is moved into the fluid cavity 920 through orifice 922. The coupling fluid exits the fluid cavity 920 through lower aperture 302 to provide acoustic coupling to an object being scanned. The coupling fluid also exits the fluid cavity through the upper aperture 908. The ultrasonic transducer 710 may be moved vertically relative to the upper chamber 102 to allow for focusing of the ultrasonic beam from the transducer. Recess 924 allows the ultrasonic transducer 710 to be moved to a position in close proximity to the object being scanned. This, in turn, allows higher frequency ultrasonic signals to be used without excessive attenuation. If the transducer if too far from the object, the reflected ultrasonic will be attenuated and more easily corrupted by noise. An extended lower surface 912 of the upper chamber may be used to create a film of coupling fluid above the object being scanned.

Figure 15:
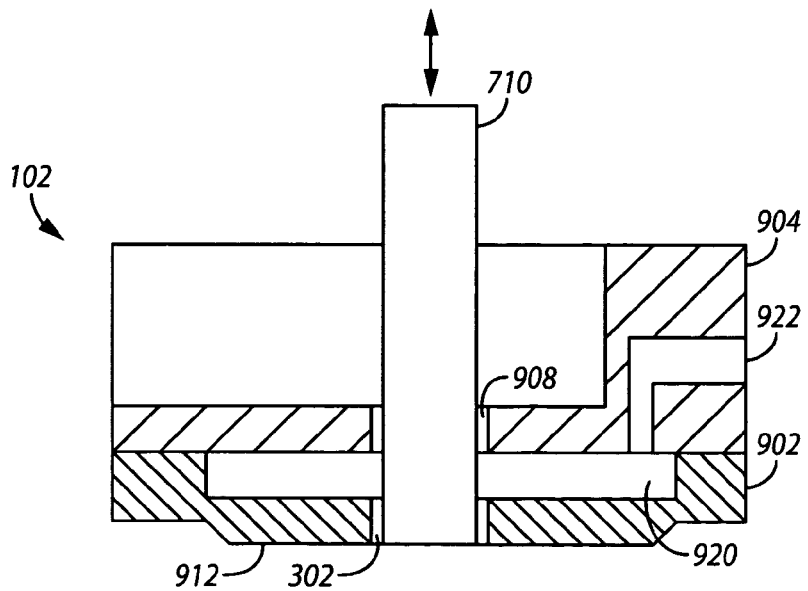
FIG. 15 is a sectional view of a further embodiment of an upper chamber.

A sectional view of a further embodiment of an upper chamber of the invention is shown in FIG. 15. Referring to FIG. 15, an ultrasonic transducer 710 is shown passing through the aperture 908 in the upper piece 904. The ultrasonic transducer 710 may be moved vertically with respect to the upper chamber 102 to allow for focusing of the ultrasonic beam at different depths in the object under test. This allows the spacing between the upper chamber 102 and part under test to be held substantially constant. A fluid cavity 920 is formed between the upper piece 904 and the lower piece 902. In operation, coupling fluid in moved into the fluid cavity 920 through fluid inlet 922. The coupling fluid exits the fluid cavity 920 through aperture 302 in the bottom of the fluid cavity and through aperture 908 in the top of the chamber. The aperture 302 is sized to accommodate the ultrasound emitting surface of the ultrasonic transducer 710, enabling the ultrasonic transducer 710 to pass through the aperture and be positioned very close to the object being scanned. This facilitates the use of very high frequency ultrasound (with frequencies from a hundred megahertz to several gigahertz or more). The ultrasound emitting surface may be positioned flush with the lower surface of the upper chamber, or may protrude below the lower surface. The lower surface of the lower piece 902 may have a lowered section 912. This lowered section 912 serves a similar purpose to the scanning bar described above (104 in FIG. 1).

In a further embodiment of the invention, the ultrasonic transducer is held at a fixed position within the upper chamber. In this embodiment, the upper chamber and the ultrasonic transducer are move together to adjust the distance between the ultrasound emitting end of the transducer and the object being scanned. In this embodiment, the upper aperture 908 may be sealed around the ultrasonic transducer.

The upper chamber 102 shown in FIGS. 9-15 is moved with the ultrasonic transducer 710 along a scanning path as an object 106 is scanned. Its use is not limited to scanning objects held in trays. It will be apparent to those of ordinary skill in the art that the upper chamber may be used in a variety of ultrasonic scanning operations to provide acoustic coupling being an ultrasonic transducer and an object being scanned. In particular, it may be used in the scanning semiconductor wafers, electronic devices and optical devices. A semiconductor wafer may be held in a wafer chuck, such as a vacuum chuck, while undergoing scanning. The wafer may be moved relative to the upper chamber during scanning or vice versa.

DRYER. After the ultrasonic scanning of the parts in the holder is completed, it is desirable to remove the coupling fluid from the parts to prevent the fluid from affecting the quality or appearance (i.e. water spots) of the parts. The dryer of the present invention includes one or more of the following:

Gas Stream. A gas stream can be used to dry any residual coupling fluid from the parts. Typically compressed and/or heated air is directed across the parts. By using a vacuum or suction from beneath the holder, drying gas will still flow across the parts but it will tend to hold the parts in the holder rather than dislodge them. Additionally, an air-knife can be used to blow residual fluid from the upper surface of the parts.

Wicking Material. If any liquid residue is left on parts, a wicking material may be placed in contact with the part to remove the moisture.

Brush. If any liquid residue is left on parts, the parts may be passed under a brush, so that bristles of the brush contact with the part and remove the moisture. Preferably, the brush contacts the lower surface of the part.

While the invention has been particularly shown and described with reference to exemplary embodiments, it will be understood by those skilled in the art that various changes in form and detail may be made therein without departing from the spirit and scope of the invention. In addition, it is evident that many alternatives, modifications, permutations and variations will become apparent to those of ordinary skill in the art in light of the foregoing description. Accordingly, it is intended that the present invention embrace all such alternatives, modifications and variations as fall within the scope of the appended claims.

What is claimed is:

1. A method for coupling ultrasound between an ultrasonic transducer and an object, the method comprising:
   positioning an upper chamber and the object in close proximity to each other, so that a planar region of a lower wall of the upper chamber is substantially parallel to an upper surface of the object;
   positioning an ultrasound emitting surface of the ultrasonic transducer in a fluid cavity of the upper chamber, the fluid cavity having a lower aperture in the planar region of the lower wall;
   moving the ultrasonic transducer relative to the upper chamber to adjust the focus of the ultrasound;
   supplying a coupling fluid to the fluid cavity so that coupling fluid flows through the lower aperture of the fluid cavity onto the object and forms a thin film of coupling fluid between the planar region of the lower wall and the upper surface of the object; and insonifying the object with ultrasound from the ultrasonic transducer.

2. A method in accordance with claim 1, further comprising moving the ultrasonic transducer and the upper chamber in a scan path substantially parallel to a surface of the object, wherein moving the ultrasonic transducer relative to the upper chamber to adjust the focus of the ultrasound comprises moving the ultrasonic transducer in a direction substantially perpendicular to the scan path.

3. A method in accordance with claim 2, further comprising adjusting the separation between the upper chamber and the object to form a thin layer of coupling fluid between a lower surface of the upper chamber and an upper surface of the object.

4. A method in accordance with claim 1, wherein the ultrasonic transducer passes through an upper aperture of the fluid cavity and further comprising flowing coupling fluid across the ultrasound emitting surface of the ultrasonic transducer to exit through the upper aperture and remove bubbles from the ultrasound emitting surface of the ultrasonic transducer.

5. A method in accordance with claim 1, further comprising collecting coupling fluid dispensed from the upper chamber in a lower chamber positioned beneath the object.

6. A method in accordance with claim 1, wherein moving the ultrasonic transducer relative to the upper chamber to adjust the focus of the ultrasound comprises moving the ultrasonic transducer through the lower aperture.

7. A method for coupling ultrasound between an ultrasonic transducer and an object, the method comprising:
   positioning an upper chamber and the object in close proximity to each other;
   positioning the ultrasonic transducer in a fluid cavity of the upper chamber, the ultrasonic transducer having an ultrasound emitting end that passes at least partially through a lower aperture in a planar region of a lower wall of the fluid cavity;
   moving the ultrasonic transducer relative to the upper chamber to adjust the focus of the ultrasound;
   supplying a coupling fluid to the fluid cavity so that coupling fluid flows through the lower aperture of the fluid cavity onto the object; and
   insonifying the object with ultrasound from the ultrasonic transducer.

8. An apparatus for coupling ultrasound to an object, comprising:
   an ultrasonic transducer having a surface operable to emit an ultrasound beam; and
   an upper chamber containing a fluid cavity bounded on one side by a lower wall, the upper chamber having a fluid inlet for receiving coupling fluid, a first aperture for receiving the ultrasonic transducer and a second aperture in the lower wall for dispensing the coupling fluid to a surface of the object;
   wherein the ultrasound emitting surface of the ultrasonic transducer is moveable within the fluid cavity to adjust a focal point of the ultrasound emitted from the surface of the ultrasonic transducer.

9. An apparatus in accordance with claim 8, wherein a portion of the lower surface of the fluid cavity is recessed to accommodate the surface of the ultrasonic transducer that is operable to emit ultrasound, thereby reducing the acoustic path length between the ultrasonic transducer and the object.

10. An apparatus in accordance with claim 8, wherein ultrasound from the ultrasonic transducer passes through the second aperture to a position close to the surface of the object.

11. An apparatus in accordance with claim 8, further comprising a linear motion device operable to move the ultrasonic transducer relative to the upper chamber.

12. An apparatus in accordance with claim 8, further comprising at least one motion actuator for moving the ultrasonic transducer and the upper chamber in a scan path substantially parallel to the surface of the object.

13. An apparatus in accordance with claim 8, wherein the object comprises a part of a plurality of parts supported in a parts tray.

14. An apparatus in accordance with claim 13, further comprising a track operable to support the parts tray and move through it through the ultrasonic beam.

15. An apparatus in accordance with claim 8, wherein the object comprises a semiconductor wafer held in wafer chuck.

16. An apparatus in accordance with claim 8, wherein the object comprises a microelectronic device.

17. An apparatus in accordance with claim 8, wherein the object comprises an optical device.

18. An apparatus in accordance with claim 8, wherein a bottom surface of the upper chamber is flat so as to constrain the coupling fluid in a thin layer between the bottom surface and of the upper chamber and an upper surface of the object when the bottom surface of the upper chamber is placed in close proximity to the object.

19. An apparatus for coupling ultrasound to an object, comprising:
   an ultrasonic transducer having a surface operable to emit an ultrasound beam;
   an upper chamber containing a fluid cavity, the upper chamber having a fluid inlet for receiving coupling fluid, a first aperture for receiving the ultrasonic transducer and a second aperture for dispensing the coupling fluid to a surface of the object; and
   a lower chamber positioned beneath the object for collecting coupling fluid dispensed from the upper chamber, wherein the ultrasound emitting surface of the ultrasonic transducer is moveable within the fluid cavity to adjust a focal point of the ultrasound emitted from the surface of the ultrasonic transducer.

20. An apparatus in accordance with claim 8, wherein the ultrasonic transducer passes through the second aperture to a position close to the object.

21. An apparatus for coupling ultrasound between an ultrasonic transducer and an object, comprising:
- a chamber adapted to substantially enclose an ultrasound transmitting surface of the ultrasonic transducer to form a fluid cavity, the fluid cavity being bounded on one side by a lower wall that is adapted to be placed in close proximity to the object;
- a fluid inlet in the fluid cavity for receiving a flow of coupling fluid;
- a first aperture for admitting the ultrasonic transducer into the fluid cavity; and
- a second aperture, located in the lower wall, for dispensing coupling fluid from the fluid cavity to the object;

wherein the first and second apertures are sized to restrict flow of coupling fluid from the fluid cavity.

22. An apparatus in accordance with claim 21, further comprising:
- an ultrasonic transducer operable to generate ultrasound; and
- a linear motion device for positioning the ultrasonic transducer relative to the chamber to facilitate focusing of the ultrasound in the object.

23. An apparatus in accordance with claim 22, wherein the ultrasound passes between the ultrasonic transducer and the object through the second aperture.

24. An apparatus in accordance with claim 22, wherein the ultrasound has a frequency greater than 100 MHz.

25. An apparatus in accordance with claim 22, wherein the ultrasound has a frequency greater than 500 MHz.

26. An apparatus in accordance with claim 21, wherein the first and second apertures are coaxially aligned.

27. An apparatus in accordance with claim 21, wherein a the lower wall of the chamber in proximity to the ultrasound transmitting surface of the ultrasonic transducer is less than 1 mm thick, allowing the ultrasound transmitting surface of the ultrasonic transducer to be placed in close proximity to the object.

28. An apparatus in accordance with claim 21, wherein a bottom surface of the chamber is flat so as to constrain the coupling fluid in a thin layer between the bottom surface of the chamber and an upper surface of the object when the bottom surface of the chamber is placed in close proximity to the object.

29. An apparatus for coupling ultrasound to an object, comprising:
- an ultrasonic transducer having a surface operable to emit an ultrasound beam;
- an upper chamber containing a fluid cavity, the upper chamber having a lower wall adapted to be positioned substantially parallel to and in close proximity to an upper surface of the object;
- a fluid inlet in the upper chamber for receiving coupling fluid into the fluid cavity;
- a first aperture in the upper chamber for receiving the ultrasonic transducer;
- and a second aperture in the lower wall for dispensing the coupling fluid to form a film of coupling fluid between the upper a surface of the object and the lower wall;

wherein the upper chamber and the ultrasonic transducer are moveable to adjust a focal point of the ultrasound emitted from the surface of the ultrasonic transducer.

30. An apparatus for coupling ultrasound to an object, comprising:
- an ultrasonic transducer having a surface operable to emit an ultrasound beam; and
- an upper chamber containing a fluid cavity, the upper chamber having a fluid inlet for receiving coupling fluid, a first aperture for receiving the ultrasonic transducer and a second aperture for dispensing the coupling fluid to a surface of the object;

wherein the upper chamber and the ultrasonic transducer are moveable to adjust a focal point of the ultrasound emitted from the surface of the ultrasonic transducer and wherein the lower wall of the chamber in proximity to the ultrasound emitting surface of the ultrasonic transducer is less than 1 mm thick, allowing the ultrasound emitting surface of the ultrasonic transducer to be placed in close proximity to the object.

31. An apparatus in accordance with claim 29, wherein the ultrasonic transducer passes through the second aperture to a position close to the object.

32. An apparatus in accordance with claim 29, wherein the second aperture is sized to restrict flow of coupling fluid from the fluid cavity.

33. A method for coupling ultrasound between an ultrasonic transducer and an object, the method comprising:
- positioning an upper chamber and the object in close proximity to each other;
- positioning an ultrasound emitting surface of the ultrasonic transducer in a fluid cavity of the upper chamber, the fluid cavity having a lower aperture extending through a lower wall of the fluid cavity;
- supplying a coupling fluid to the fluid cavity so that coupling fluid flows through the lower aperture of the fluid cavity onto the object to form a thin layer of coupling fluid between the lower wall of the fluid cavity and an upper surface of the object;
- moving the ultrasonic transducer relative to the upper chamber to adjust the focus of the ultrasound whilst maintaining the thickness of the thin layer of coupling fluid between the lower wall of the fluid cavity and the upper surface of the object; and
- insonifying the object with ultrasound from the ultrasonic transducer.

* * * * *